United States Patent [19]

Worrell et al.

[11] Patent Number: 4,931,214
[45] Date of Patent: Jun. 5, 1990

[54] OXIDIC BODIES WITH IONIC AND ELECTRONIC CONDUCTIVITY

[75] Inventors: Wayne Worrell, Norbeth, Pa.; Werner Weppner; Helmut Schubert, both of Stuttgart, Fed. Rep. of Germany

[73] Assignee: Max-Planck-Gesellschaft zur Foerderung der Wissenschaften e.V., Goettingen, Fed. Rep. of Germany

[21] Appl. No.: 186,764

[22] Filed: Apr. 22, 1988

Related U.S. Application Data

[63] Continuation of Ser. No. 782,554, Oct. 1, 1985, abandoned.

[30] Foreign Application Priority Data

Oct. 5, 1984 [DE] Fed. Rep. of Germany ....... 3436597

[51] Int. Cl.$^5$ ............................................. H01B 1/06
[52] U.S. Cl. .................................... 252/520; 501/103; 501/104
[58] Field of Search ................. 501/103, 104; 252/520

[56] References Cited

U.S. PATENT DOCUMENTS

| 1,127,578 | 2/1915 | Baldwin | 252/520 |
| 2,108,544 | 2/1938 | Meyer | 252/520 |
| 2,905,564 | 9/1959 | Roup et al. | 501/104 |
| 3,268,349 | 8/1966 | Brixner | 252/520 |
| 3,303,033 | 2/1967 | La Grange et al. | 501/104 |
| 3,373,119 | 3/1968 | Krystymak | 252/520 |
| 3,398,923 | 8/1968 | Pipitz et al. | 501/152 |
| 3,410,728 | 11/1968 | Fullman et al. | 501/103 |
| 3,522,064 | 7/1970 | Valdsaar | 501/103 |
| 4,406,699 | 9/1983 | Beck et al. | 501/103 |
| 4,753,902 | 6/1988 | Ketcham | 501/87 |

FOREIGN PATENT DOCUMENTS

115148 8/1984 European Pat. Off. .
482720 4/1967 France .

OTHER PUBLICATIONS

Journal of American Ceramic Society, No. 5/6, 6-5-77, pp. 262-267.
Journal of Mat'l. Science, Bond 14, No. 1, 1979, pp. 59-65.
Chem. Abstracts, Nr. 24, Jun. 15, 1970, p. 359.

Primary Examiner—William R. Dixon, Jr.
Assistant Examiner—Deborah Jones
Attorney, Agent, or Firm—Felfe & Lynch

[57] ABSTRACT

The present invention provides a mixed conducting body, wherein it consists of 98 to 25 mol % of cubic or tetragonal zirconium dioxide, 1.5 to 25 mol % of an oxide stabilizing the zirconium dioxide phase and 0.5 to 50 mol % of at least one oxide of a metal of Group Va and VIa of the Periodic System of Elements and/or titanium dioxide, as well as the usual impurities.

This body is outstandingly useful as electrode material for oxygen exchange reactions.

19 Claims, 9 Drawing Sheets

OXIDIC BODIES WITH IONIC AND ELECTRONIC CONDUCTIVITY

This application is a continuation of application Ser. No. 782,554, filed Oct. 1, 1985, now abandoned.

The present invention is concerned with oxidic bodies with ionic and electronic conductivity and with the use thereof, especially as electrode material for oxygen exchange reactions.

Oxygen electrodes normally consist of platinum or other metallic conducting materials, such as mixed oxides with perovskite structure, which are stable in the air and in other oxidising atmospheres. In the case of electrodes of such metallic conducting materials, the charge transmission takes place on the unidimensional boundary lines of the three-phase contact gas-electrode-electrolyte and thus, for example, in the case of a fuel cell thus on a triple contact platinum/fuel gas/hydrogen gas. However, in the case of such a contact, porous materials, for example porous platinum, as well as operating at high temperatures, are necessary.

It is also known to use as electrolytes solid oxygen ion conductors based on zirconium dioxide. However, a decisive disadvantage of the use of such solid oxygen ion conductors is the necessity of a relatively high operating temperature of more than 600° C. The reason for this is the velocity-determining kinetics of the introduction and removal of oxygen on the electrodes. The steps from the oxygen molecule via the atom to the ion and the introduction thereof into the crystal lattice are limited. The ion conductivity of the zirconium oxide crystal would theoretically admittedly permit a use at markedly lower temperatures if the kinetics of the exchange of the oxygen were quick enough. However, because of the low exchange flow density, with zirconium dioxide solid electrolytes and the hitherto used electrodes, a correct indication of the electromotive force is not obtained if the oxygen partial pressures are fixed on both sides. Correspondingly constructed fuel cells do not display the desired high voltage and provide too low a current in the case of temperatures lower than 600° C.

Therefore, it is an object of the present invention to provide bodies which are suitable as electrode material with which the above-mentioned disadvantages can be overcome. This object is achieved according to the present invention.

Thus, according to the present invention, there is provided an oxidic body with ionic and electronic conductivity, wherein it consists of 98 to 25 mol % of cubic or tetragonal zirconium dioxide, 1.5 to 25 mol % of an oxide stabilising the zirconium dioxide phase and 0.5 to 50 mol % of at least one oxide of a metal of Groups Va and VIa of the (European) Periodic System of Elements (i.e. Group Va: vanadium, niobium, and tantaluym; Group VIa: chromium, molybdenum, and tungsten) and/or titanium dioxide, as well as the usual impurities.

The oxide (stabiliser) stabilising the zirconium dioxide phase is preferably an oxide of the group consisting of the alkaline earth metals, yttrium and/or the rare earth metals and is especially an oxide of the rare earth metals, yttrium oxide ($Y_1O_3$), magnesium oxide and/or calcium oxide, yttrium oxide, magnesium oxide and calcium oxide being especially preferred. The mixed conductive body according to the present invention preferably contains the stabilisers in an amount of from 5 to 15 mol.%.

Of the oxides of a metal of Groups Va and VIa and/or titanium dioxide present in an amount of from 0.5 to 50 mol %, titanium dioxide is preferably used; the oxidic bodies according to the present invention preferably contain these oxides in an amount of from 1 to 35 and especially of from 1 to 20 mol %. In an especially preferred embodiment, the oxidic material according to the present invention contains 77 to 88 mol % zirconium dioxide, 11 to 13 mol % yttrium oxide and 1 to 10 mol % titanium dioxide.

In the mixed conductive oxidic body with ionic and electronic conductivity, the zirconium dioxide is present in the cubic or tetragonal phase. As impurities, it can contain hafnium dioxide ($HfO_2$) and has a degree of purity of, for example, 95 to 99.5% and especially of from 98 to 99%. The doping which takes place by the addition of the oxides stabilising the zirconium dioxide phase is responsible for the ion conductivity; thus, due to these oxides, besides the zirconium dioxide phase-stabilising action, there is also achieved the doping necessary for the ion conductivity. The oxides of the Groups Va and VIa and/or especially titanium dioxide contribute to the electronic conductivity.

If the oxidic bodies according to the present invention are used as zirconium dioxide solid electrodes, then good results are also achieved in the temperature range below 600° C. We have found that, in the case of the use of the bodies according to the present invention as electrodes, the EMF is correctly indicated after the oxygen partial pressure has been fixed by gases or metal oxide mixtures on both sides. Furthermore, greater current densities can be achieved. Thus, electrodes produced from bodies according to the present invention make possible a substantially more uninhibited incorporation and release of oxygen into and from the crystal lattice. The incorporation of the oxygen is catalytically activated by the increased electronic conductivity of the oxidic material according to the present invention. The kinetics are even more favourable in comparison with the previously usual expensive platinum which is often used as catalyst. Therefore, oxygen probes, fuel cells, electrolysis cells, for example water electrolysis cells, or oxygen sensors, can be operated at temperatures which are lower than those previously necessary. Besides a simpler handling, thermodynamic advantages are thereby also achieved. Thus, for example, carbon can only be burnt completely to carbon dioxide below about 600° C. because, in the case of higher temperatures, the equilibrium lies considerably more strongly on the side of carbon monoxide. However, the material conversion is thereby also markedly smaller. With the use of the oxidic bodies according to the present invention, with which it is also possible to operate below 600° C., these disadvantages can be avoided. However, also in the case of working at higher temperatures, thus for example in the case of working above 600° C., with the oxidic bodies according to the present invention, for example in the case of their use as electrode materials for oxygen exchange reactions, especially as oxygen concentration cells, oxygen probes, for example for the production of steel, or for combustion motors in motor vehicles, fuel cells and electrolysis cells, advantages are achieved because the use of expensive porous platinum is thereby no longer necessary. Since, in the case of the oxidic bodies according to the present invention, the incorporation of the oxygen and the electron exchange can take place on a two-dimensional surface, in comparison with electrodes previously known, in the case of which the charge transfer takes place on unidimensional boundary lines of the three-phase contact, further constructional possibilities are possible in the construction and operation of electrolysis cells.

Consequently, the present invention is also concerned with the use of the oxidic bodies according to the present invention as electrode materials for oxygen exchange reactions, especially in oxygen concentration cells, oxygen probes, fuel cells and electrolysis cells.

The production of the oxidic bodies according to the present invention with ionic and electronic conductivity can, depending upon the intended purpose of use, take place in known manner from oxidic powdered materials The production of sinter formed bodies (sinter ceramics) can take place, for example, by mixing and grinding the oxidic components, subsequent pressing and sintering of the green body obtained in the air. The pressing thereby preferably takes place isostatically, it being especially preferred to operate at pressures of from 600 to 700 MPa.

Although the production of sintered ceramics is especially preferred for special uses, for example for high temperature fuel cells in the case of which a gas-tight electrode is necessary, the bodies according to the present invention are not limited thereto. Any other method of production is also possible, for example by mixing the powdered components in the presence of an appropriate binding agent, for example one based on silicates, such as waterglass, or of synthetic resins which do not influence the electrode properties, for example based on epoxides. Formed bodies produced in this manner can, if necessary, be made gas-tight by the subsequent application of a gas-tight coating or by a surface sintering. Further possibilities are, for example, also a production of the formed bodies by single crystal production, by compressing under high pressure without the use of high temperatures, by adhesion (whereby, however, the conductivity must be maintained) or by precipitation, or appropriate processes for the production of solid solutions of the oxidic components in zirconium dioxide. In certain cases, a foam-like consistency, for example by foaming with a synthetic resin which simultaneously serves as a binding agent, can be appropriate. As a rule, the grain sizes of the powdered components are below 120 μm. and especially below 80 μm. and are preferably from 1 to 60 μm.

The following Examples are given for the purpose of illustrating the present invention:

EXAMPLE 1

As starting materials for the production of an oxidic body according to the present invention, there were used zirconium dioxide powder with a particle size of from 1 to 40 μm. (99% $ZrO_2+HfO_2$; type SC 20 of Magnesium-Electron-MEL, England); yttrium oxide ($Y_2O_3$) (99.99%; from Ventron, Karlsruhe) and titanium dioxide (LAB quality, No. 808, from Merck, Darmstadt).

The oxides (a) 87 mol% (79.3 wgt%) zirconium dioxide, 12 mole% (20.1 wgt%) yttrium oxide and 1 mol% (0.6 wgt%) titanium dioxide; and (b) 78 mole % (73.2 wgt%) zirconium dioxide, 12 mole% yttrium oxide and 10 mole% (6 wgt%) titanium dioxide, were ground in an attrition device for up to 6 hours in n-hexane or alcohol. The slurries wee dried in the air at 70° C. and sieved through a sieve with a mesh size of 200 μm. The powder was pressed isostatically for 1 minute at a pressure of 640 MPa. The green density was 60% of the theoretical density. The samples were sintered in the air at 1550° C. for 2 hours. The samples had a diameter of 12 to 13.3 mm. and a thickness of 2.5 to 3.5 mm.

For carrying out electrical measurements (resistance and conductivity measurements), platinum paste (from the firm Demetron, Hanau() was applied to the surfaces of the samples and then heated to 500° C. for 2 hours in order to remove the organic solvent. The temperature was then increased to 800° C. and heating carried out at this temperature for 6 hours.

The alternating current resistance was measured by the complex impedance technique and the electronic conductivity by the use of a polarisation cell according to Wagner (cf. W. Weppner, J. Elektroanal, Chem., 84, 334/1977).

EXAMPLE 2

As described in Example 1, the following oxides were ground in the given mole ratio for 6 hours in an attrition device in the presence of n-hexane and then worked up as described in Example 1 to give formed bodies with a size of from 12 to 13.3 mm. diameter and 2.5 to 3.5 mm. thickness (the statements of amount are given in mol %):

(a) 30 $ZrO_2$, 20 $Y_2O_3$, 50 $TiO_2$
(b) 88 $ZrO_2$, 11 MgO, 1 $TiO_2$
(c) 88 $ZrO_2$, 8 $Y_2O_3$, 3 CaO, 1 $TiO_2$
(d) 88 $ZrO_2$, 8 $Y_2O_3$, 3 CaO, 1 $VO_2$.

Conductivity and resistance measurements were carried out as described in Example 1 on the formed bodies obtained according to (a) to (d).

FIGS. 1 to 9 of the accompanying drawings show the results of the resistance and conductivity measurements obtained with the formed bodies of Example 1.

Figure 1:
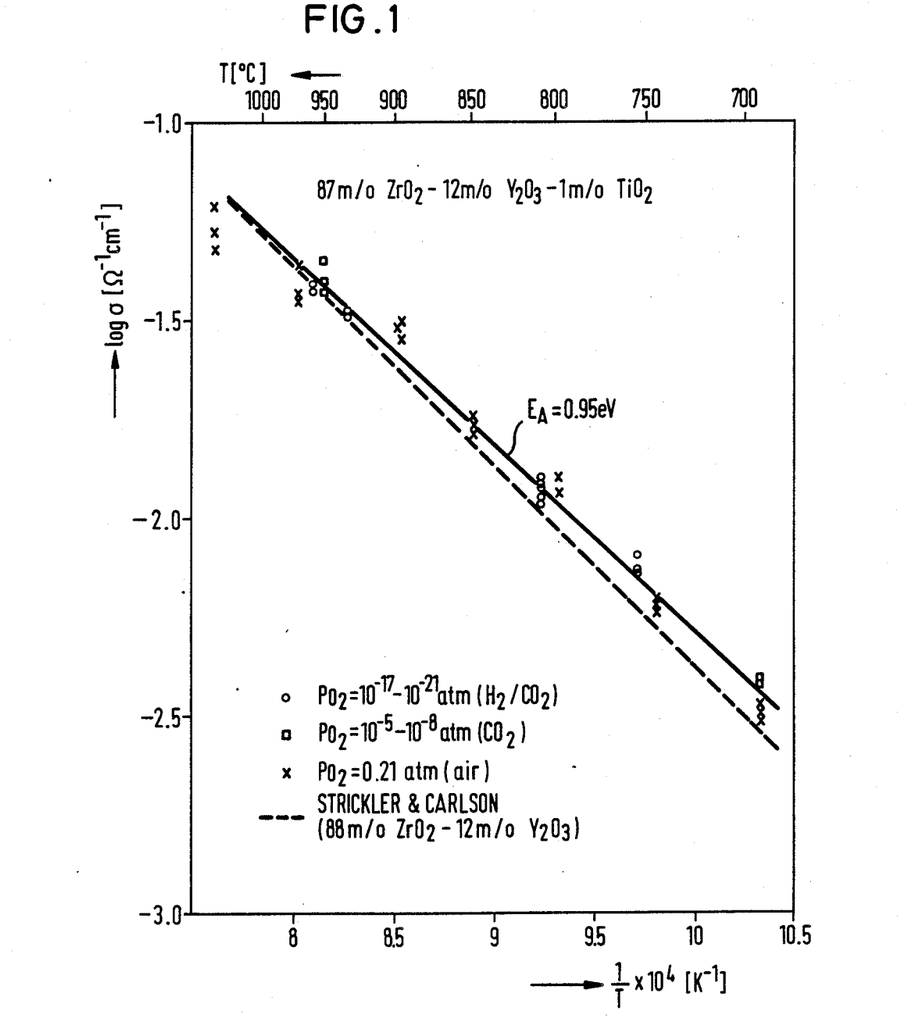
FIGS. 1 and 2 show the results of the conductivity measurements of samples (a) and (b) of Example 1 (1 and 10 mol % titanium dioxide, respectively). Within the limits of experimental measurement exactitude, the results are independent of the oxygen pressure in the region of from 0.21 to $10^{-21}$ ats.
Figure 2:
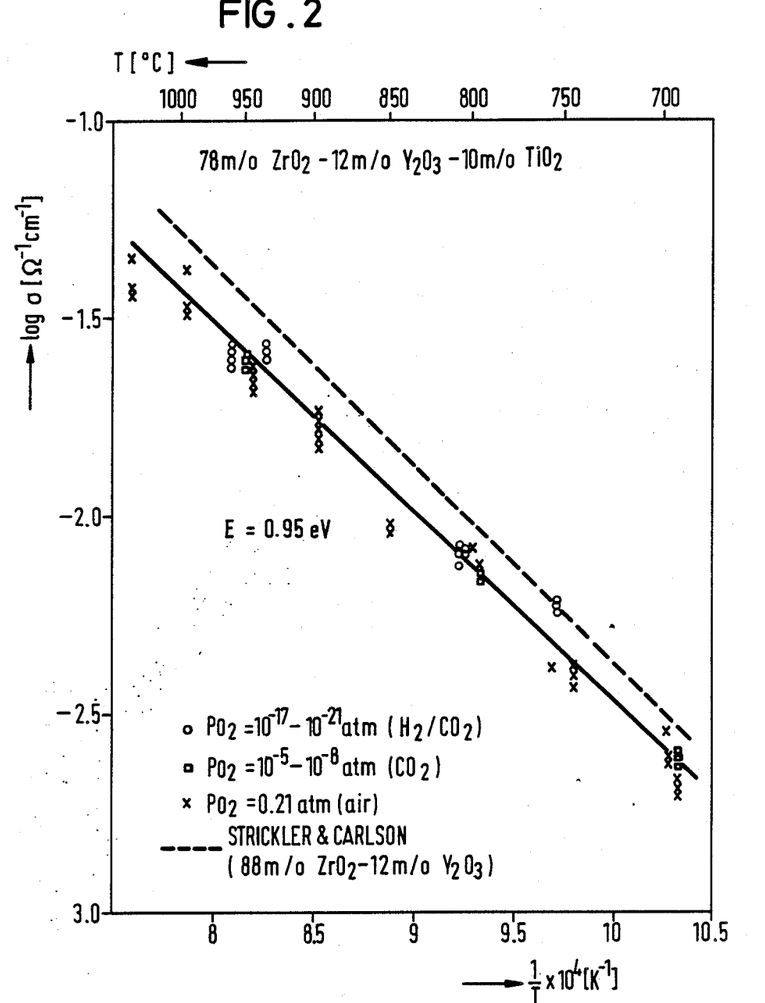
Figure 3:
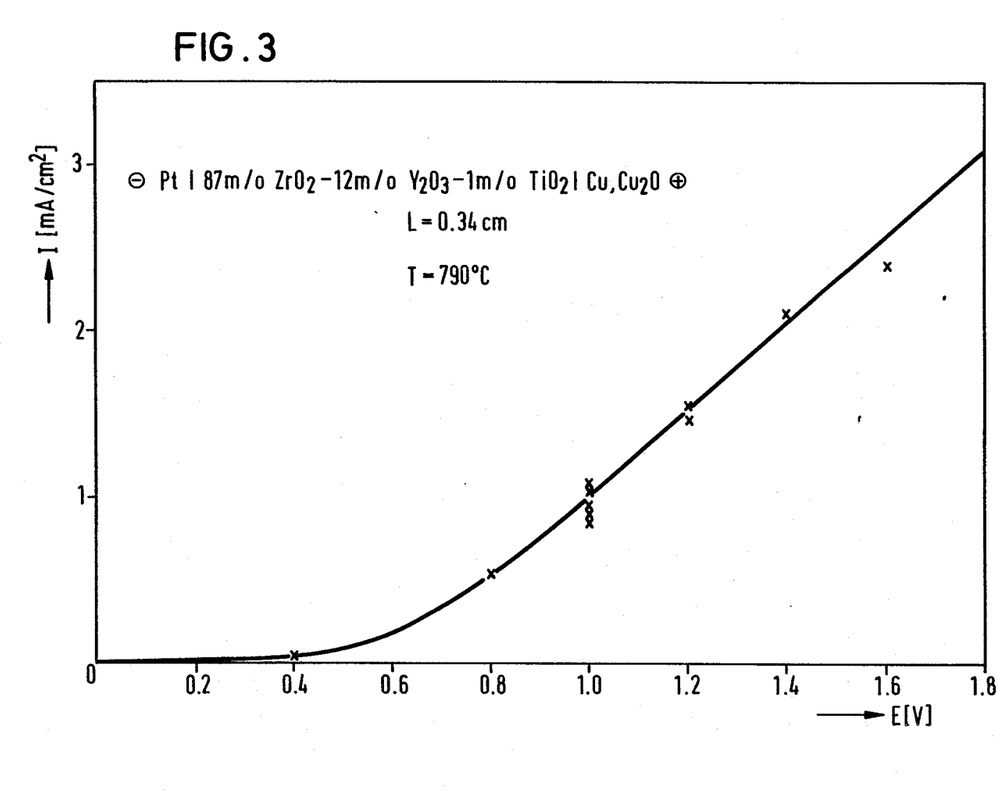
FIGS. 3 to 6 show the current strength-voltage curves of the samples according to Example 1 (a) and 1 (b) (1 mol % and 10 mol % titanium dioxide, (0.6 –6.1 wgt.%) respectively) at 697, 790 and 900° C.
Figure 4:
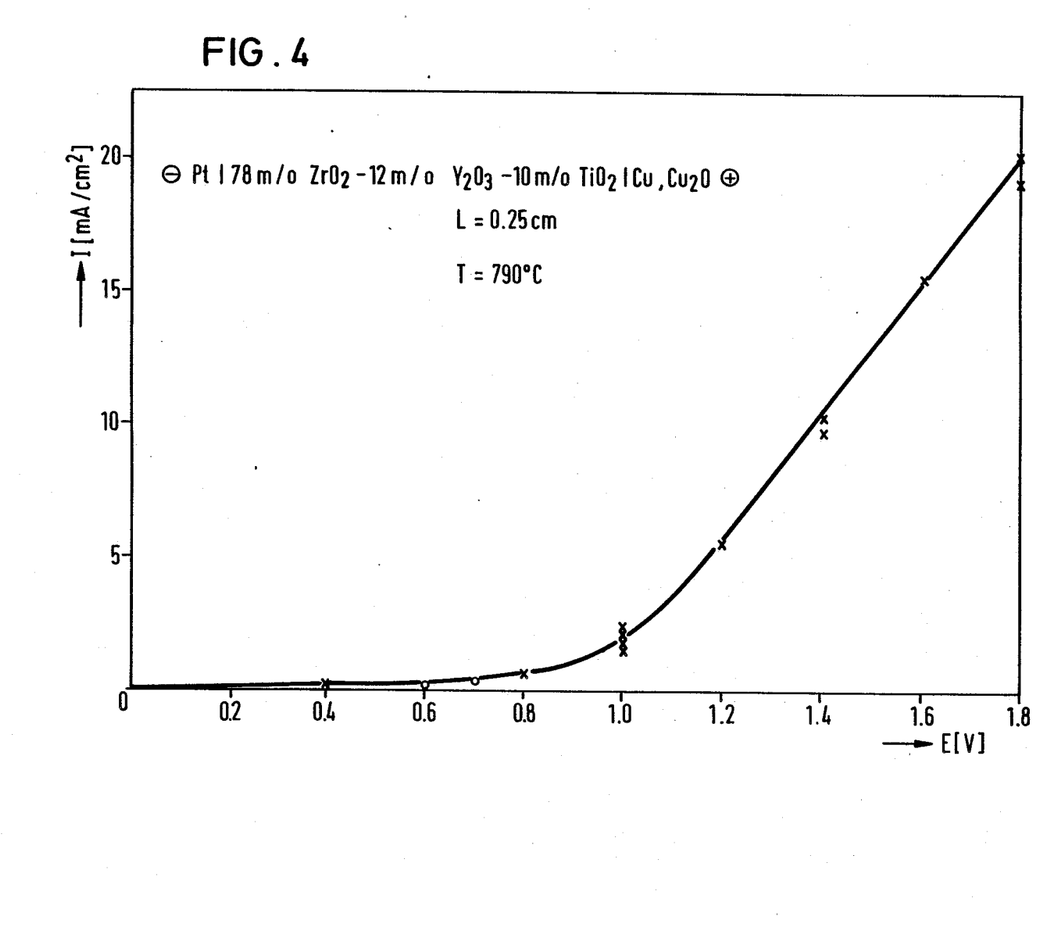
Figure 5:
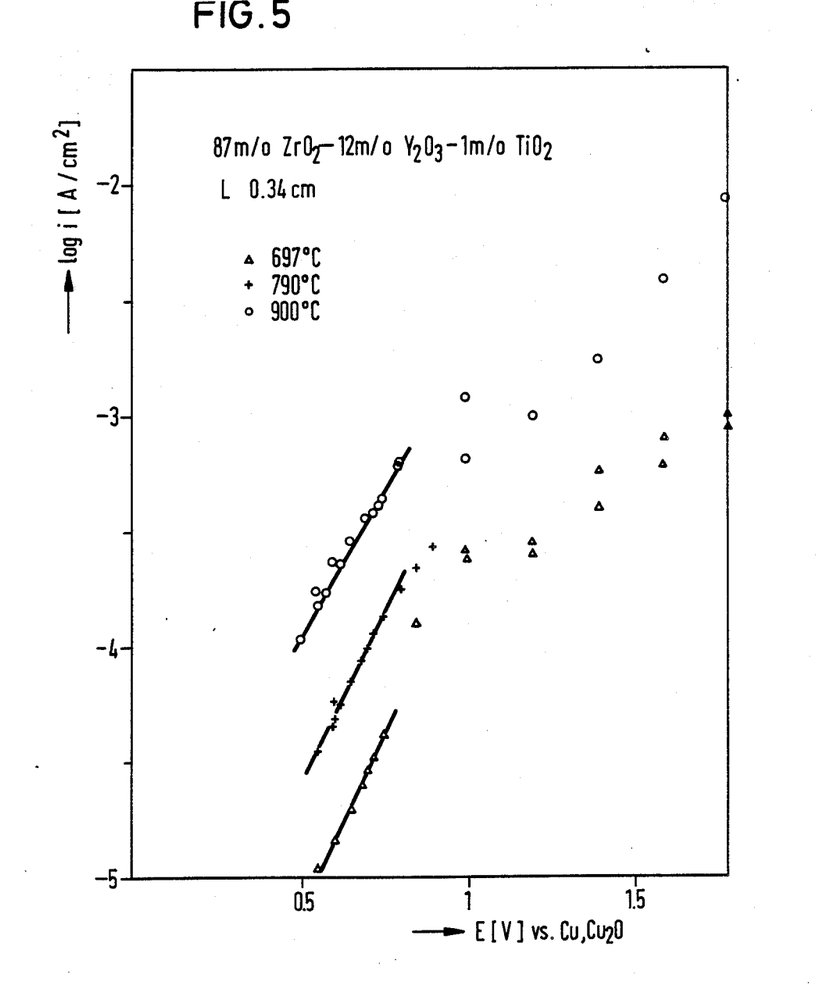
Figure 6:
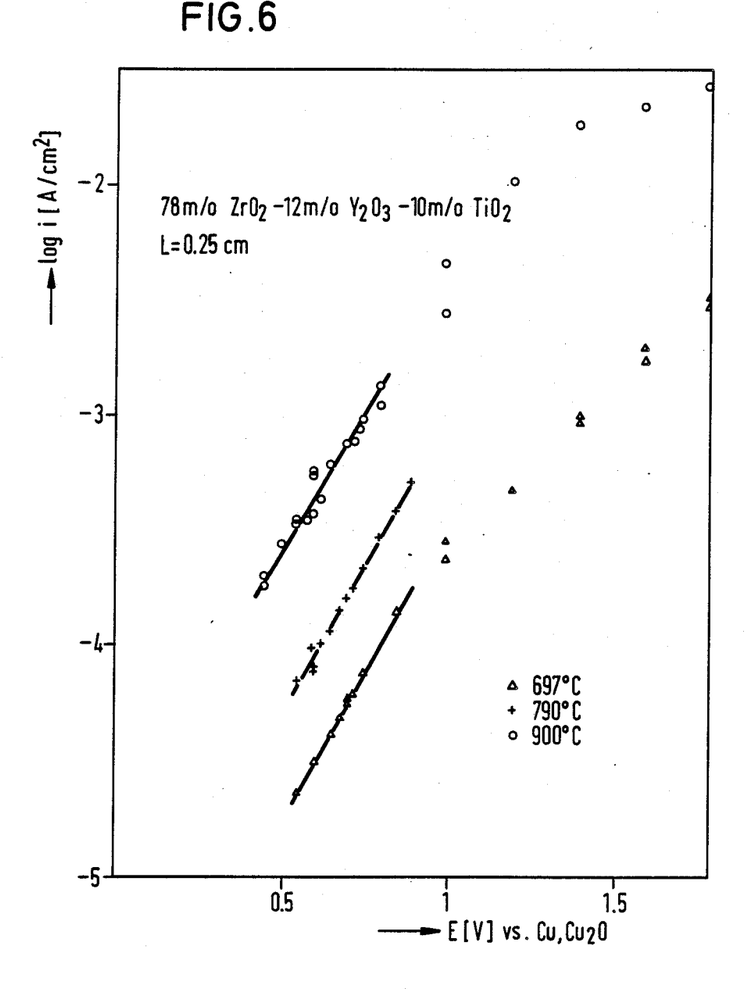
Figure 7:
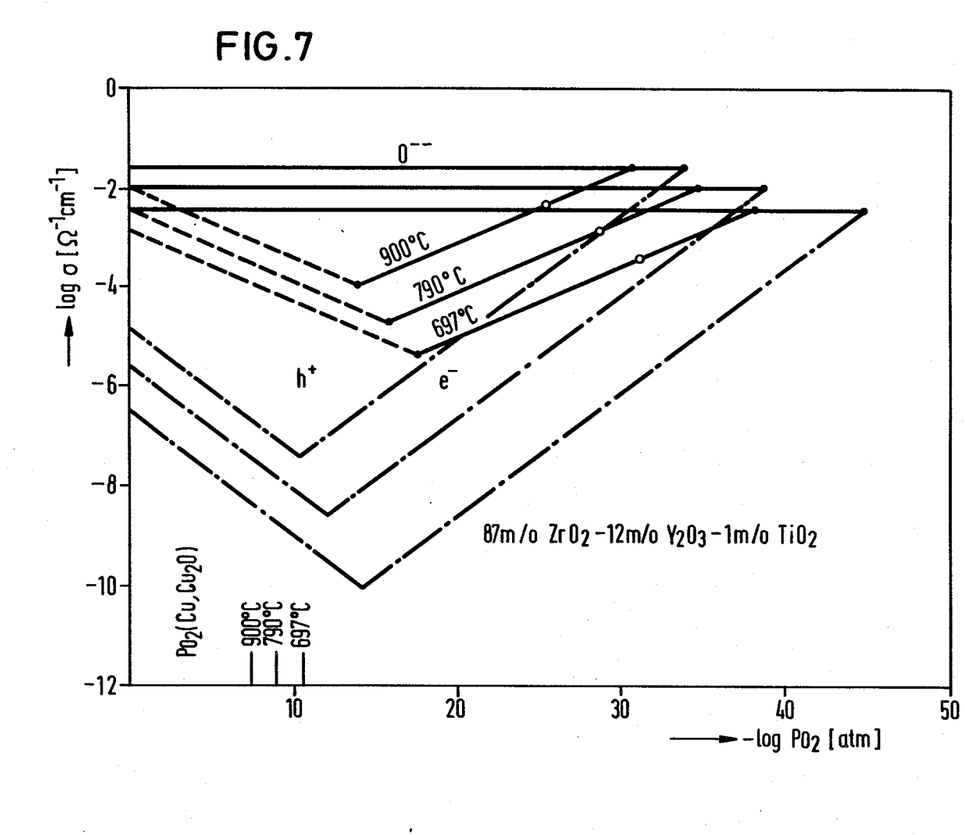
FIGS. 7 and 8 show the partial electron conductivities as function of the oxygen partial pressure, as well as the total (ion) conductivity at temperatures of 697, 790 and 900° C. For comparison, there are given the electron conductivities of a body of 88 mol % zirconium dioxide (80 wgt.%) and 12 mol % yttrium oxide (20 wgt.%).
Figure 8:
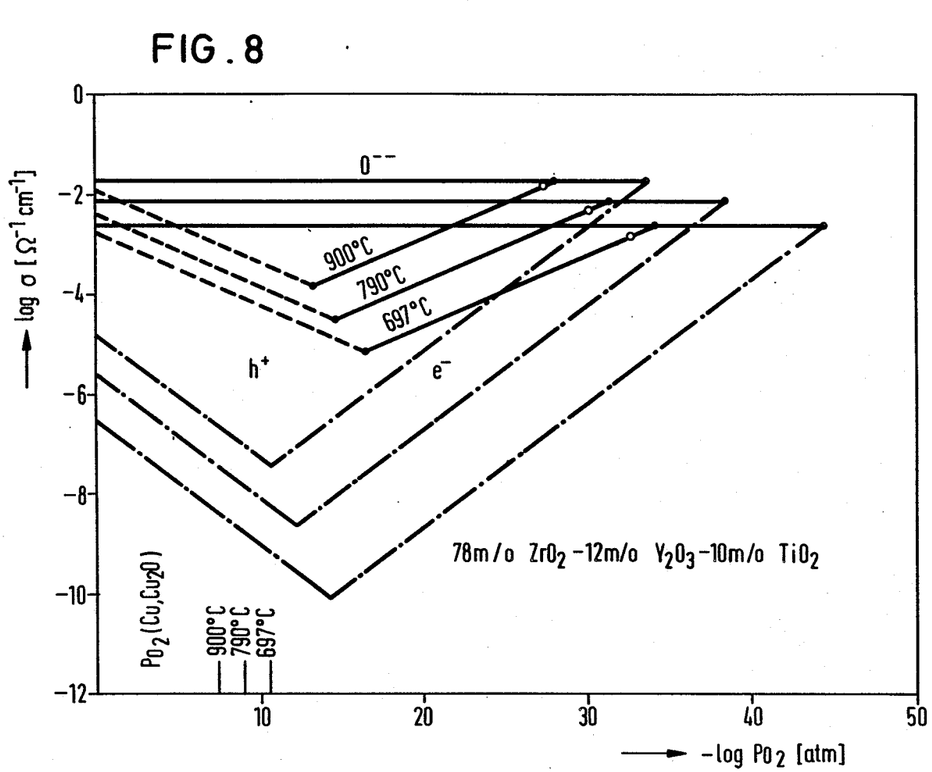
Figure 9:
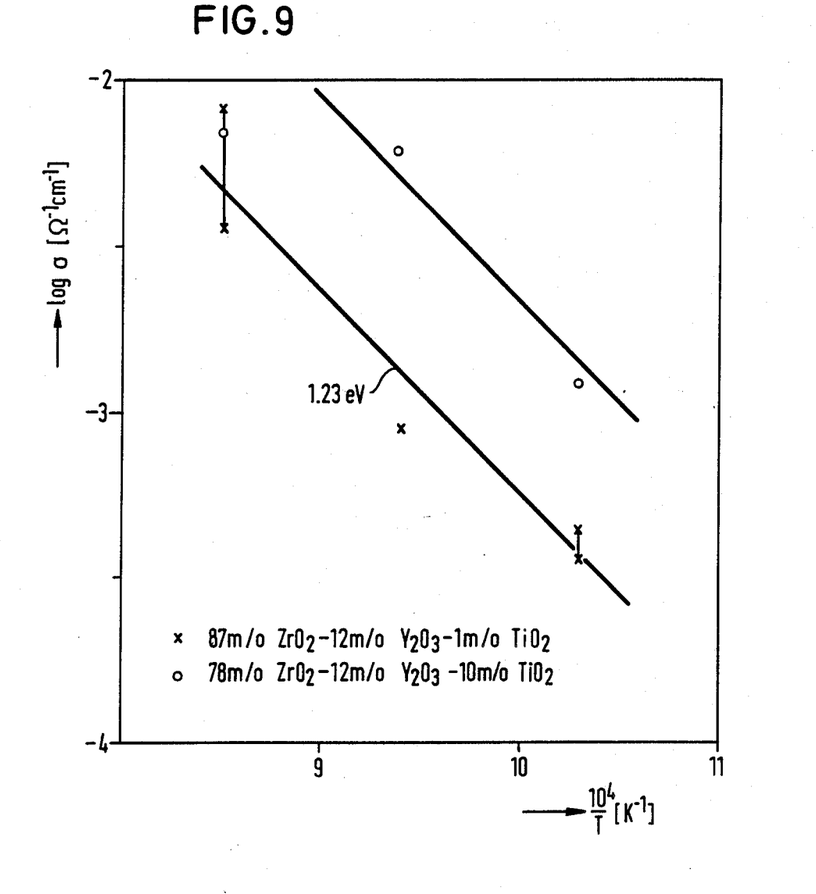
FIG. 9 shows the temperature dependence of the conductivity of the samples of Example 1 (a) and 1 (b) (1 mol % and 10 mol % titanium dioxide, (0.6 to 6.1 wgt.%) respectively) which was derived from the straight-lined parts of the curves of FIGS. 3 to 6.

We claim:
1. A mixed conductive oxidic body having a conductivity independent of oxygen pressure consisting of both ionic and electronic conductivity comprising:
   98 to 25 mole-% of cubic or tetragonal zirconium dioxide;
   1.5 to 25 mole-% of an oxide stabilizing the zirconium dioxide phase; and
   .5 to 50 mole-% of at least one oxide of a metal of Group Va and VIa of the Periodic System of Elements, titanium dioxide or a mixture thereof.

2. The mixed conductive body of claim 1 wherein the metal is selected from the group consisting of vanadium, niobium, tantalum, chromium, molybdenum and tungsten.

3. The mixed conductive body of claim 1 wherein the metal is vanadium.

4. The mixed conductive oxidic body of claim 1 wherein the body comprises a single phase solid solution of
- 98 to 25 mole-% of cubic or tetragonal zirconium dioxide;
- 1.5 to 25 mole-% of an oxide stabilizing the zirconium dioxide phase; and
- .5 to 50 mole-% of at least one oxide of a metal of Group Va and VIa of the Periodic System of Elements, titanium dioxide or a mixture thereof.

5. The mixed conductive oxidic body of claim 4 wherein the metal is selected from the group consisting of vanadium, niobium, tantalum, chromium, molybdenum and tungsten.

6. The mixed conductive oxidic body of claim 1 wherein the oxide stabilizing the zirconium dioxide phase consists of a rare earth oxide, yttrium oxide, magnesium oxide, calcium oxide or a mixture thereof.

7. The mixed conductive oxidic body of claim 1 containing 5 to 15 mole-% of the oxide stabilizing the zirconium dioxide phase.

8. The mixed conductive oxidic body of claim 1 comprising 77 to 88 mole-% zirconium dioxide; 11 to 13 mole-% yttrium oxide; and 1 to 15 mole-% titanium dioxide.

9. The mixed conductive oxidic body of claim 6 containing 5 to 15 mole-% of the oxide stabilizing the zirconium dioxide phase.

10. The mixed conductive oxidic body of claim 1 containing
- 30 mole-% zirconium dioxide (30.3wt.-%)
- 20 mole-% yttrium oxide (37 wt.-%)
- 50 mole-% titanium dioxide (32.7 wt.-%).

11. The mixed conductive oxidic body of claim 1 containing
- 88 mole-% zirconium dioxide (80.9 wt.-%)
- 11 mole-% magnesium oxide (18.5 wt.-%)
- 1 mole-% titanium dioxide (0.6 wt.-%).

12. The mixed conductive oxidic body of claim 1 containing 88 mole-% zirconium dioxide (84.1 wt.-%)
- 8 mole-% yttrium oxide (14 wt.-%)
- 3 mole-% calcium oxide (1.3 wt.-%)
- 1 mole-% titanium dioxide (1.6 wt.-%).

13. The mixed conductive oxidic body of claim 1 containing
- 88 mole-% zirconium dioxide (84.1 wt.-%)
- 8 mole-% yttrium oxide (14 wt.-%)
- 3 mole-% calcium oxide (1.3 wt.-%)
- 1 mole-% vanadium dioxide (0.6 wt.-%).

14. The mixed conductive oxidic body of claim 1 having an electrical resistivity not in excess of from about 10 to 150 ohm-cm at about 800° C.

15. An electrode material for oxygen exchange reactions comprising the mixed conductive oxidic body of claim 1.

16. The electrode material of claim 15 having 77 to 88 mole-% zirconium dioxide, 9 to 13 mole-% yttrium oxide and 1 to 10 mole-% titanium dioxide.

17. The electrode material of claim 13 wherein the metal is vanadium.

18. The electrode material of claim 17 wherein the oxide stabilizing the zirconium dioxide phase is yttrium oxide.

19. A mixed conductive oxidic body having a conductivity independent of oxygen pressure consisting of both ionic and electronic conductivity comprising:
- 98 to 25 mole-% of cubic or tetragonal zirconium dioxide;
- 1.5 to 25 mole-% of an oxide stabilizing the zirconium dioxide phase; and
- .5 to 50 mole-% of titanium dioxide.

* * * * *

UNITED STATES PATENT AND TRADEMARK OFFICE
CERTIFICATE OF CORRECTION

PATENT NO.  : 4,931,214

DATED       : June 5, 1990

INVENTOR(S) : Wayne Worrell et al

It is certified that error appears in the above-identified patent and that said Letters Patent is hereby corrected as shown below:

Column 1, line 64, "$Y_1O_3$" should read --$Y_2O_3$--.

Column 3, line 62 after "%" (second occurrence) insert --(20.7 wgt%)--.

Column 4, line 6, "Hanau()" should read --Hanau)--.

Column 6, line 10, "1.6" should read --0.6--.

Column 6, line 26, "13" should read --15--.

Signed and Sealed this

Nineteenth Day of May, 1992

Attest:

DOUGLAS B. COMER

Attesting Officer

Acting Commissioner of Patents and Trademarks